(12) United States Patent
Kim et al.

(10) Patent No.: US 7,504,261 B2
(45) Date of Patent: Mar. 17, 2009

(54) METHOD FOR HIGHLY SENSITIVE NUCLEIC ACID DETECTION USING NANOPORE AND NON-SPECIFIC NUCLEIC ACID-BINDING AGENT

(75) Inventors: Kui-hyun Kim, Daejeon-si (KR); Jun-hong Min, Yongin-si (KR); In-ho Lee, Yongin-si (JP); Ah-gi Kim, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 7 days.

(21) Appl. No.: 11/414,022

(22) Filed: Apr. 28, 2006

(65) Prior Publication Data

US 2006/0292605 A1 Dec. 28, 2006

(30) Foreign Application Priority Data

Jun. 27, 2005 (KR) .................... 10-2005-0055904

(51) Int. Cl.
*G01N 33/00* (2006.01)
*G01N 33/53* (2006.01)
*C07H 21/04* (2006.01)

(52) U.S. Cl. .................... 436/94; 436/806; 536/23.1

(58) Field of Classification Search ...................... None
See application file for complete search history.

(56) References Cited

U.S. PATENT DOCUMENTS

| 6,309,886 | B1 * | 10/2001 | Ambrose et al. ............... 436/63 |
| 6,362,002 | B1 | 3/2002 | Denison et al. |
| 6,428,959 | B1 | 8/2002 | Deamer |
| 6,723,513 | B2 * | 4/2004 | Lexow .......................... 435/6 |
| 2003/0104428 | A1 | 6/2003 | Branton et al. |
| 2006/0287833 | A1 * | 12/2006 | Yakhini ........................ 702/20 |
| 2007/0172386 | A1 * | 7/2007 | Li et al. ........................ 422/58 |

* cited by examiner

*Primary Examiner*—Bradley L Sisson
(74) *Attorney, Agent, or Firm*—Cantor Colburn LLP

(57) ABSTRACT

Provided is a method of sensitively detecting nucleic acids in a nucleic acid sample, the method comprising: contacting the sample comprising the nucleic acid with a non-specific nucleic acid binding agent in an electrically conductive fluid medium; contacting the sample comprising the nucleic acid bound to the agent with a nanopore; and applying a voltage to the nanopore and monitoring a current change through the nanopore. The nucleic acid can be sensitively detected because a change in current amplitude through the nanopore is greater than when nucleic aid detection is performed without using an intercalator.

2 Claims, 5 Drawing Sheets

(A)

(B)

NATIVE LAMBDA DNA

YOYO- DNA COMPLEX

NATIVE LAMBDA DNA

YOYO- DNA COMPLEX

| | Lambda DNA | | YOYO + Lambda DNA |
| --- | --- | --- | --- |
| | 300mV | 600mV | 300mV |
| Amplitude (pA) | ~ 350 | ~ 600 | ~ 800 |

METHOD FOR HIGHLY SENSITIVE NUCLEIC ACID DETECTION USING NANOPORE AND NON-SPECIFIC NUCLEIC ACID-BINDING AGENT

CROSS-REFERENCE TO RELATED PATENT APPLICATION

This application claims the benefit of Korean Patent Application No. 10-2005-0055904, filed on Jun. 27, 2005, in the Korean Intellectual Property Office, the disclosure of which is incorporated herein in its entirety by reference.

BACKGROUND OF THE INVENTION

1. Field of the Invention

The present invention relates to a method for highly sensitive nucleic acid detection using a nanopore and a non-specific nucleic acid-binding agent.

2. Description of the Related Art

Various methods of detecting a target biomolecule in a sample have been reported. A method using nanopores is widely used in a highly sensitive DNA detecting system, which is an imitation of a bio-pore system, and is capable of sequencing bases in nucleic acids.

A method of characterizing individual polymer molecules based on monomer-interface interactions is disclosed in U.S. Pat. No. 6,362,002. In this method, a single-stranded nucleic acid polymer can pass through a channel in an interface between two pools, but a double-stranded nucleic acid polymer cannot pass through the channel, and can thus be detected.

A method of determining the presence of double-stranded nucleic acids in a sample is disclosed in U.S. Pat. No. 6,428,959. Double-stranded nucleic acid can be detected by translocating nucleic acids in a sample through a nanopore, monitoring a current amplitude through the nanopore during the translocation, and measuring the duration of a transient blockade of current. However, U.S. Pat. No. 6,428,959 does not disclose a method of detecting nucleic acids using a non-specific nucleic acid-binding agent to increase a current amplitude.

A method for the characterization of nucleic acid molecules is disclosed in U.S. Patent Publication No. 2003/0104428. A maximum change in a signal can be achieved by changing specific local areas using proteins specific to nucleotide sequences. However, U.S. Patent publication No. 2003/0104428 relates to the detecting of DNA having a specific sequence using nanopore, and does not disclose the detecting of nucleic acids using a non-specific nucleic acid-binding agent to increase a current amplitude.

The inventors of the present invention discovered that a nucleic acid can be accurately detected by increasing a current amplitude change through nanopores using a non-specific nucleic acid binding agent, regardless of specific sequences.

SUMMARY OF THE INVENTION

The present invention provides a method of sensitively detecting nucleic acids in a nucleic acid sample. The method includes: contacting the sample including the nucleic acid with a non-specific nucleic acid binding agent in an electrically conductive fluid medium; contacting the sample including the nucleic acid bound to the agent with a nanopore; and applying a voltage to the nanopore and monitoring a current change through the nanopore.

The present invention also provides an apparatus for detecting nucleic acids. The apparatus includes: a nanopore; a non-specific nucleic acid binding agent; a device applying a voltage across the nanopore; and a detector monitoring a current change through the nanopore.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1A:
FIG. 1 illustrates a measured current through a nanopore using only an intercalator without lambda DNA.

A method of sensitively detecting nucleic acids in a sample according to an embodiment of the present invention includes: contacting the sample including the nucleic acid with a non-specific nucleic acid binding agent in an electrically conductive fluid medium; contacting the sample including the nucleic acid bound to the agent with a nanopore; and applying a voltage across the nanopore and monitoring a current change through the nanopore.

The nucleic acid is sensitively detected by increasing the current amplitude that is generated when the nucleic acid is passed through the nanopore using the non-specific nucleic acid binding agent. Specifically, the volume of the nucleic acid bound to the non-specific nucleic acid binding agent and the current flowing therethrough are greater than when the nucleic acid is not bound to the agent.

The sample including the nucleic acid is contacted with the non-specific nucleic acid binding agent in the electrically conductive fluid medium. The use of the non-specific nucleic acid binding agent allows the sensitive detection of the nucleic acid through the increase in the current amplitude during the transfer of the nucleic acid through the nanopore. The nucleic acid to be detected exists in the fluid sample, especially in the liquid sample. The sample should be dissolved in an electrically conductive solvent since the sample should be electrically conductive. Any electrically conductive solvent can be used. The solvent is water soluble and may be pure water or water containing at least one additional substance, for example, a buffer, or a salt such as KCl. The pH of the fluid sample may be about 6.0 to 9.0, for example, about 7.0 to 8.5.

The sample including the nucleic acid bound to the agent is contacted with the nanopore. The nanopore is a structure having a channel or pore with a diameter of nano dimensions. The terms "nanopore" and "channel" are used interchangeably herein to refer to a structure having a nano-sized passage through which the nucleic acid can pass.

The current change through the nanopore is monitored through the application of the voltage across the nanopore. The nucleic acid in the fluid sample is transferred through the nanopore due to the applied voltage. The current amplitude through the nanopore is monitored during the transfer. The nucleic acid can be effectively detected from the monitored current since the change in the current amplitude is related to the passage of the nucleic acid through the nanopore.

The nucleic acid in the sample can be transferred through the nanopore using a convenient method, for example, by applying the electrical field to the sample. The voltage is sufficiently strong to move the nucleic acid through the nanopore.

The time required to apply the voltage across the fluid sample depends on the amount of the transferred nucleic acid. In general, the voltage may be applied for 1 ms or longer, preferably 1 s or longer, or more preferably 10 s or longer, even more preferably 1 min or longer. However, the voltage is not applied for longer than 10 min or 1 hour.

The non-specific nucleic acid binding agent may be an intercalator, a major groove binding agent or a minor groove binding agent. The agent binds to the nucleic acid and may increase the current amplitude by increasing a volume change of the nucleic acid.

The intercalator may include YOYO (1,1'-[1,3-propanediylbis[(dimethyliminio)-3,1-propanediyl]]bis[4-[(3-methyl-2(3H)-benzoxazolyli dene)methyl]]-,tetraiodide), TOTO (1-1'-[1,3-propanediylbis[(dimethyliminio)-3,1-propanediyl]]bis[4-[(3-methyl-2(3H)-ben zothiazolylidene)methyl]]-,tetraiodide) and Ethidium Bromide (EtBr).

The intercalator may be anything that can be inserted into the nucleic acid, but is not limited thereto. However, it is preferable that the intercalator may increase the current amplitude by increasing the volume change of the nucleic acid. The formula of YOYO is as follows.

applying the voltage across the nanopore, and monitoring the current change through the nanopore with the detector.

The nanopore is a structure having a channel or pore with a diameter of nano dimensions, and may be synthetic or natural. Natural nanopores include oligomeric protein channels such as porin, gramicidine and synthetic peptide, for example, a heptameric channel self-assembled of α-hemolysine. Synthetic nanopores include passageways bored through solid materials.

The device applying the voltage across the nanopore can produce a voltage of 10 mV or greater, preferably 50 mV or greater, and more preferably, 100 mV or greater. In general, the device includes a silver chloride electrode connected to a source of a voltage supply.

The detector monitoring the current change through the nanopore includes a low noise amplifier, a current injector and an analog to digital (A/D) converter. The detector may include other elements for an output generating system using data acquisition software and including an electronic storage medium, etc.

The non-specific nucleic acid binding agent may be an intercalator, a major groove binding agent or a minor groove binding agent. The material may increase the current amplitude by increasing a volume change of the nucleic acid.

The intercalator may include YOYO (1,1'-[1,3-propanediylbis[(dimethyliminio)-3,1-propanediyl]]bis[4-[(3-methyl-2(3H)-benzoxazolyli dene)methyl]]-,tetraiodide),

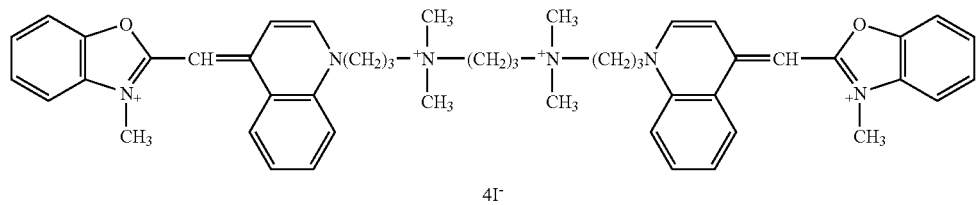

The nanopore may have a diameter ranging from 1.5 nm to 120 nm. When the diameter is less than 1.5 nm, the nucleic acid cannot pass through the nanopore, and when the diameter is greater than 120 nm, the nucleic acid can not be detected because the change in current amplitude is too small.

The voltage may range from 100 mV to 1000 mV. When the voltage is less than 100 mV, a passage efficiency of the nucleic acid through the nanopore is too low, and when the voltage is greater than 1000 mV, noise is too great.

The electrically conductive fluid medium includes multiple nucleic acids containing different sequences. According to an embodiment of the present invention, not only one, but also many types of nucleic acids having different lengths or sequences can be detected. Nucleic acids having different lengths or sequences can be detected since the monitored current amplitude change varies according to the type of the nucleic acid.

An apparatus for detecting nucleic acids according to another embodiment of the present invention includes: a nanopore; a non-specific nucleic acid binding agent; a device applying a voltage across the nanopore; and a detector monitoring a current change through the nanopore.

The nucleic acid can be sensitively detected by contacting the sample including the nucleic acid with the non-specific nucleic acid binding agent in an electrically conductive fluid medium, introducing the bound sample to the apparatus, TOTO (1-1'-[1,3-propanediylbis[(dimethyliminio)-3,1-propanediyl]]bis[4-[(3-methyl-2(3H)-ben zothiazolylidene)methyl]]-,tetraiodide) and Ethidium Bromide (EtBr). The intercalator may be anything that can be inserted into the nucleic acid, but is not limited thereto. However, it is preferable that the intercalator may increase the current amplitude by increasing the volume change of the nucleic acid.

The nanopore may have a diameter ranging from 1.5 nm to 120 nm. When the diameter is less than 1.5 nm, the nucleic acid cannot pass through the nanopore, and when the diameter is greater than 120 nm, the nucleic acid can not be detected because the change in current amplitude is small.

The voltage may range from 100 mV to 1000 mV. When the voltage is less than 100 mV, a passage efficiency of the nucleic acid through the nanopore is too low, and when the voltage is greater than 1000 mV, noise is too great.

The present invention will be described in greater detail with reference to the following examples. The following examples are for illustrative purposes and are not intended to limit the scope of the invention.

EXAMPLE 1

Preparing a Nanopore

A nanopore was prepared according to the following procedures. A high stress nitride layer was formed to a thickness of 250-300 nm on the front surface of a silicon wafer using a low pressure chemical vapor deposition (LPCVD) device and the back surface of the silicon wafer was coated with a photoresist. The result was patterned into 600 μm×600 μm units.

Next, when the silicon wafer was etched using KOH, 600 μm×600 μm of the pattern on the back surface was etched and then the nitride layer on the front surface of the silicon wafer was etched. Thus, a 30 μm×30 μm nitride membrane window was prepared.

A hole having a diameter of about 100 nm was prepared on the nitride membrane window using a focused ion beam (FIB) after washing the nitride membrane window with an organic solvent. Then, the surface was treated using atomic layer deposition (ALD).

EXAMPLE 2

Measuring Current Change without Nucleic Acids

Figure 1B:
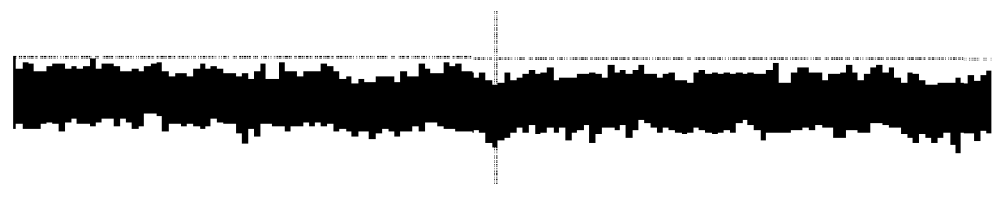

Current through a nanopore was measured when an intercalator was used, and not lambda DNA. 0.1 μM of YOYO-1 was used as the intercalator, 1 M KCl, and 10 mM Tris-EDTA (pH 8.0) were used as the electrically conductive fluid medium, and a voltage of 300 mV was applied to the nanopore prepared in Example 1 with a diameter of 100 nm. FIG. 1 illustrates the measured current through the nanopore using only the intercalator without lambda DNA. A and B in FIG. 1 indicate measurements for duplicate of the nanopores prepared in Example 1. As illustrated in FIG. 1, there was little change in the current when using only the intercalator without DNA.

EXAMPLE 3

Measuring Current Change with Lambda DNA

Figure 2A:
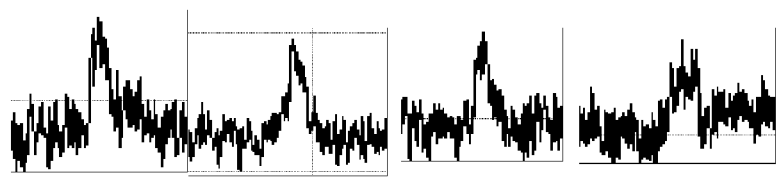
FIG. 2 illustrates a measured current through a nanopore A in Example 2 using the intercalator with lambda DNA.
Figure 2B:
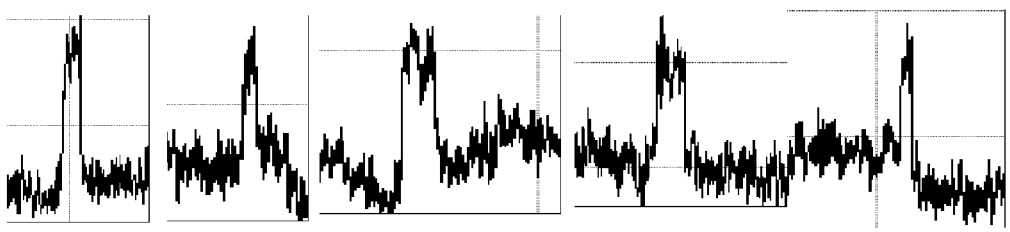

Current through a nanopore was measured when an intercalator with lambda DNA was used. 0.1 μM of YOYO-1 was used as the intercalator, 0.1 nM of lambda DNA was used, 1 M KCl, and 10 mM Tris-EDTA (pH 8.0) were used as the electrically conductive fluid medium, and a voltage of 300 mV was applied to the nanopore prepared in Example 1 with a diameter of 100 nm. FIG. 2 illustrates the measured current through the nanopore A in Example 2 using the intercalator with lambda DNA. As illustrated in FIG. 2, while the current amplitude of the native lambda DNA through the nanopore was about 200 pA, the current amplitude of the YOYO-DNA complex through the nanopore was about 800 pA. The current amplitude was found to have increased four times with the YOYO-DNA complex to which YOYO-1 was added as the intercalator compared with the native lambda DNA.

Figure 3A:
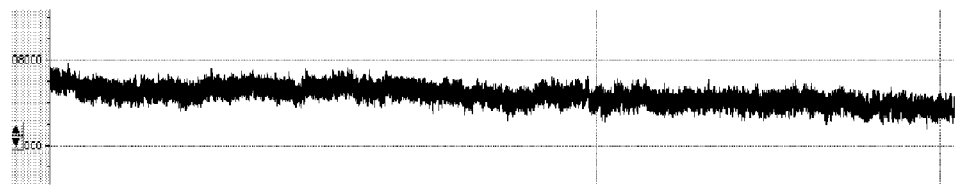
FIG. 3 illustrates a measured current through a nanopore B in Example 2 using the intercalator with lambda DNA.
Figure 3B:
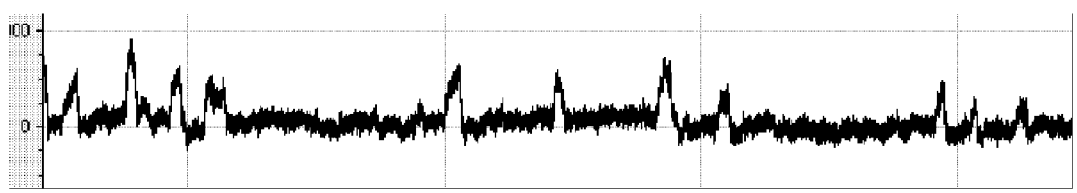

FIG. 3 illustrates the measured current through the nanopore B in Example 2 using the intercalator with lambda DNA. As illustrated in FIG. 3, while the current amplitude through the nanopore was hardly detected for the native lambda DNA, the current amplitude through the nanopore was about 880 pA for the YOYO-DNA complex. Thus, the current amplitude was found to increase remarkably for the YOYO-DNA complex to which YOYO-1 was added as the intercalator compared with the native lambda DNA.

Therefore, the nucleic acid can be detected more sensitively with the intercalator as indicated by the remarkable increase in the current amplitude over the case when the intercalator was not used.

EXAMPLE 4

Measuring Current Change According to Strength of Applied Voltage

Figure 4A:
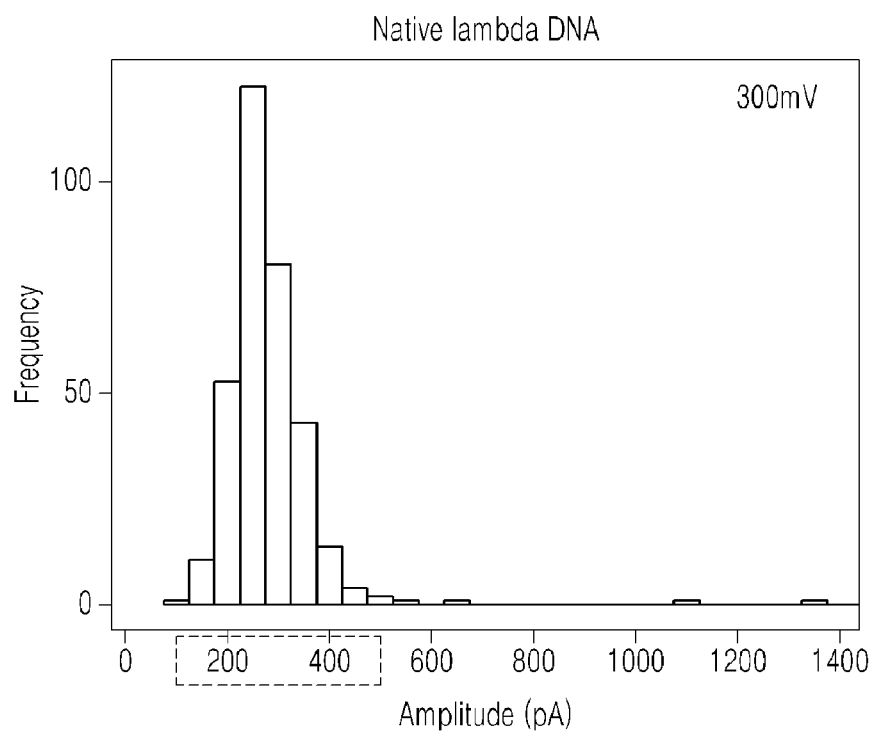
FIG. 4 illustrates a measured current through the nanopore A in Example 2 according to an applied voltage.
Figure 4B:
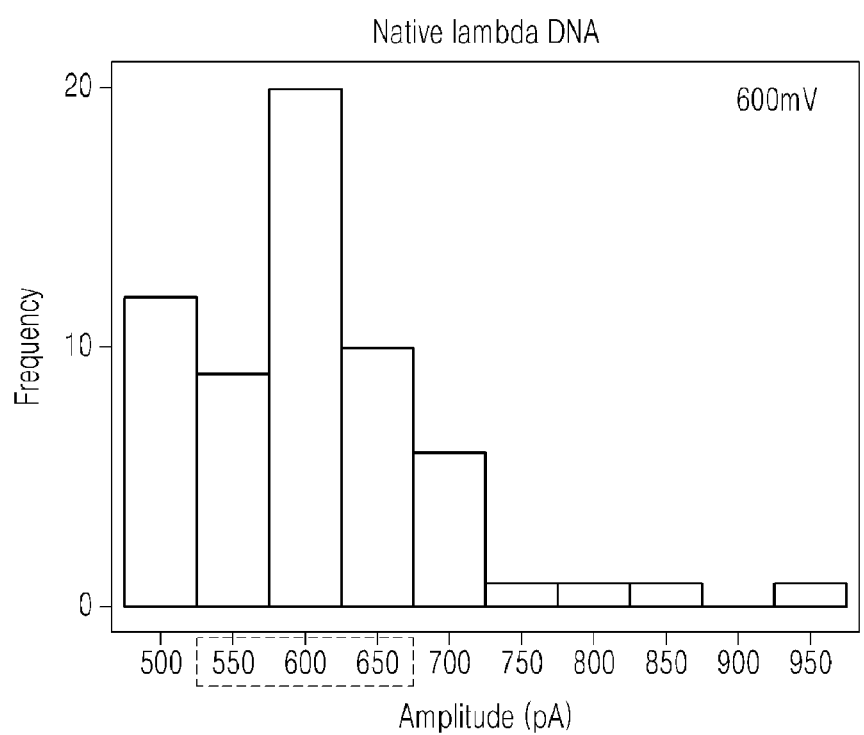
Figures 4C, 4D:
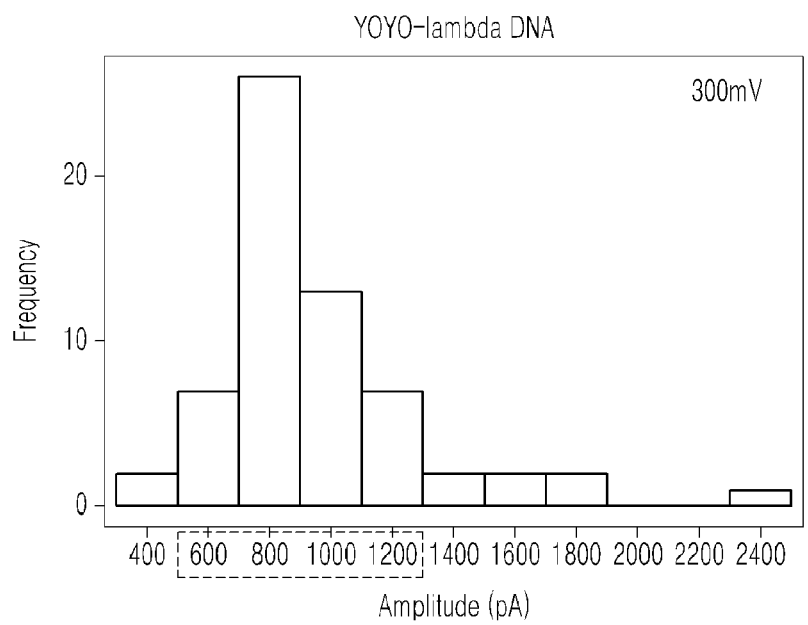

The current through a nanopore was measured according to the strength of an applied voltage. 0.1 μM of YOYO-1 was used as the intercalator, 0.1 nM of lambda DNA was used, 1 M KCl and 10 mM Tris-EDTA (pH 8.0) were used as the electrically conductive fluid medium, and 300 mV was applied to the nanopore prepared in Example 1 with a diameter of 100 nm. FIG. 4 illustrates the measured current through the nanopore A in Example 2 according to the strength of the applied electrical field. As illustrated in FIG. 4, while the current amplitude through the nanopore was about 350 pA for the native lambda DNA when the voltage was 300 mV, the current amplitude through the nanopore was about 600 pA when the voltage was 600 mV. Also, the current amplitude through the nanopore was about 800 pA for the YOYO-DNA complex when the voltage was 300 mV, and which was higher than 600 pA measured when 600 mV was applied for the native lambda DNA. Thus, the results show that a method of using the intercalator is more effective than a method of using the voltage increase to increase the current amplitude.

According to the present invention, the nucleic acid can be detected more sensitively using the change in current amplitude through the nanopore when the intercalator is used according to the present invention than when no intercalator is used as in the conventional art.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of detecting nucleic acids in a nucleic acid sample, the method comprising:

contacting a sample comprising a nucleic acid with a non-specific nucleic acid binding agent in an electrically conductive fluid medium, wherein the non-specific nucleic acid binding agent is an intercalator selected from the group consisting of YOYO (1,1'-[1,3-propanediylbis[(dimethyliminio)-3,1-propanediyl]]bis[4-[(3-methyl-2(3H)-benzoxazolylidene) methyl]]-,tetraiodide), TOTO (1-1'-[1,3-propanediylbis [(dimethyliminio)-3,1-propanediyl]]bis[4-[(3-methyl-2 (3H)-benzothiazolylidene)methyl]]-,tetraiodide) and Ethidium Bromide (EtBr);

contacting the sample comprising the nucleic acid bound to the non-specific nucleic acid binding agent with a nanopore, wherein the nanopore has a diameter ranging from 1.5 nm to 120 nm; and applying a voltage across the nanopore, wherein the voltage ranges from 100 mV to 1000 mV; and detecting nucleic acids by detecting an increase in current through the nanopore.

2. The method of claim 1, wherein the electrically conductive fluid medium comprises multiple nucleic acids comprising different sequences.

* * * * *